United States Patent
Babaev

(10) Patent No.: US 6,960,173 B2
(45) Date of Patent: *Nov. 1, 2005

(54) ULTRASOUND WOUND TREATMENT METHOD AND DEVICE USING STANDING WAVES

(76) Inventor: Eilaz Babaev, 5564 Bimini Dr., Minnetonka, MN (US) 55343

( * ) Notice: Subject to any disclaimer, the term of this patent is extended or adjusted under 35 U.S.C. 154(b) by 463 days.

This patent is subject to a terminal disclaimer.

(21) Appl. No.: 09/774,145

(22) Filed: Jan. 30, 2001

(65) Prior Publication Data
US 2002/0103448 A1 Aug. 1, 2002

(51) Int. Cl.⁷ ............................................. A61N 7/00
(52) U.S. Cl. ........................................ 601/2; 604/22
(58) Field of Search .................... 601/2–4; 604/22; 600/439

(56) References Cited

U.S. PATENT DOCUMENTS

| | | |
|---|---|---|
| 3,275,059 A | 9/1966 | McCullough |
| 3,392,916 A | 7/1968 | Engstrom et al. |
| 3,561,444 A | 2/1971 | Boucher |
| 3,860,173 A | 1/1975 | Sata |
| 4,052,004 A | 10/1977 | Martin et al. |
| 4,085,893 A | 4/1978 | Durley, III |
| 4,153,201 A | 5/1979 | Berger et al. |
| 4,251,031 A | 2/1981 | Martin et al. |
| 4,271,705 A | 6/1981 | Crostack |
| 4,294,407 A | 10/1981 | Reichl et al. |
| 4,301,093 A | 11/1981 | Eck |
| 4,301,968 A | 11/1981 | Berger et al. |
| 4,309,989 A | 1/1982 | Fahim |
| 4,319,155 A | 3/1982 | Nakai et al. |
| 4,334,531 A | 6/1982 | Reichl et al. |
| 4,352,459 A | 10/1982 | Berger et al. |
| 4,428,531 A | 1/1984 | Martin |
| 4,466,571 A | 8/1984 | Muhlbauer |
| 4,530,360 A | 7/1985 | Duarte |
| 4,541,564 A | 9/1985 | Berger et al. |
| 4,582,654 A | 4/1986 | Karnicky et al. |
| 4,619,400 A | 10/1986 | Van Der Burgt |
| 4,642,581 A | 2/1987 | Erickson |
| 4,655,393 A | 4/1987 | Berger |
| 4,659,014 A | 4/1987 | Soth et al. |
| 4,679,551 A | 7/1987 | Anthony |
| 4,726,523 A | 2/1988 | Kokubo et al. |
| 4,726,525 A | 2/1988 | Yonekawa et al. |
| 4,733,820 A | 3/1988 | Endo et al. |
| 4,756,478 A | 7/1988 | Endo et al. |

(Continued)

FOREIGN PATENT DOCUMENTS

EP          0 156 4009 A2       2/1985

(Continued)

OTHER PUBLICATIONS

Journal of Burn Care & Rehabilitation; vol. 21, No. 4; Jul./Aug. 2000 pp. 333–338.

(Continued)

*Primary Examiner*—Ruth S. Smith
(74) *Attorney, Agent, or Firm*—Carter, DeLuca, Farrell & Schmidt, LLP.

(57) ABSTRACT

The method and device of the present invention for wound treatment with ultrasound standing waves includes a transducer probe to produce ultrasonic waves. The ultrasonic transducer has a tip with a distal radiation surface that radiates ultrasound energy toward the surface of a wound. Ultrasound standing waves occurring as a result of incident and reflected waves from the wound surface create ultrasonic radiation pressure. Ultrasound radiation pressure increases the blood flow in wound area, and ultrasound waves kill bacteria, stimulate healthy tissue cell and treat wounds.

12 Claims, 2 Drawing Sheets

U.S. PATENT DOCUMENTS

| | | |
|---|---|---|
| 4,783,003 A | 11/1988 | Hirabayashi et al. |
| 4,790,479 A | 12/1988 | Matsumoto et al. |
| 4,793,339 A | 12/1988 | Matsumoto et al. |
| 4,850,534 A | 7/1989 | Takahashi et al. |
| 4,877,989 A | 10/1989 | Drews et al. |
| 4,905,671 A | 3/1990 | Senge et al. |
| 4,930,700 A | 6/1990 | McKown |
| 4,941,618 A | 7/1990 | Hildebrand et al. |
| 4,961,885 A | 10/1990 | Avrahami et al. |
| 5,002,059 A | 3/1991 | Crowley et al. |
| 5,040,537 A | 8/1991 | Katakura |
| 5,063,922 A | 11/1991 | Hakkinen |
| 5,076,266 A | 12/1991 | Babaev |
| 5,104,042 A | 4/1992 | McKown |
| 5,115,805 A | 5/1992 | Bommannan et al. |
| 5,134,993 A | 8/1992 | van der Linden et al. |
| 5,163,433 A | 11/1992 | Kagawa et al. |
| 5,172,692 A | 12/1992 | Kulow et al. |
| 5,186,162 A | 2/1993 | Talish et al. |
| 5,197,946 A | 3/1993 | Tachibana |
| 5,211,160 A | 5/1993 | Talish et al. |
| 5,231,975 A | 8/1993 | Bommannan et al. |
| 5,269,291 A | 12/1993 | Carter |
| 5,315,998 A | 5/1994 | Tachibana et al. |
| 5,316,000 A | 5/1994 | Chapelon et al. |
| 5,318,014 A | 6/1994 | Carter |
| 5,323,769 A | 6/1994 | Bommannan et al. |
| 5,324,255 A | 6/1994 | Passafaro et al. |
| 5,345,940 A | 9/1994 | Seward et al. |
| 5,347,998 A | 9/1994 | Hodson et al. |
| 5,362,309 A | 11/1994 | Carter |
| 5,374,266 A | 12/1994 | Kataoka et al. |
| 5,380,411 A | 1/1995 | Schlief |
| 5,393,296 A | 2/1995 | Rattner |
| 5,431,663 A * | 7/1995 | Carter .................. 606/128 |
| 5,437,606 A | 8/1995 | Tsukamoto |
| 5,515,841 A | 5/1996 | Robertson et al. |
| 5,515,842 A | 5/1996 | Ramseyer et al. |
| 5,516,043 A | 5/1996 | Manna et al. |
| 5,520,166 A | 5/1996 | Ritson et al. |
| 5,520,612 A | 5/1996 | Winder et al. |
| 5,527,350 A | 6/1996 | Grove et al. |
| 5,529,572 A | 6/1996 | Spector |
| 5,545,124 A | 8/1996 | Krause et al. |
| 5,551,416 A | 9/1996 | Stimpson et al. |
| 5,554,172 A | 9/1996 | Horner et al. |
| 5,556,372 A | 9/1996 | Talish et al. |
| 5,573,497 A | 11/1996 | Chapelon |
| 5,616,140 A | 4/1997 | Prescott |
| 5,626,554 A | 5/1997 | Ryaby et al. |
| 5,643,179 A | 7/1997 | Fujimoto |
| 5,656,016 A | 8/1997 | Ogden |
| 5,658,323 A | 8/1997 | Miller |
| 5,699,805 A | 12/1997 | Seward et al. |
| 5,707,402 A | 1/1998 | Heim |
| 5,707,403 A | 1/1998 | Grove et al. |
| 5,730,705 A | 3/1998 | Talish et al. |
| 5,735,811 A | 4/1998 | Brisken |
| 5,743,863 A | 4/1998 | Chapelon |
| 5,752,924 A | 5/1998 | Kaufman et al. |
| 5,762,616 A | 6/1998 | Talish |
| 5,785,972 A | 7/1998 | Tyler |
| 5,835,678 A | 11/1998 | Li et al. |
| 5,843,139 A | 12/1998 | Goedeke et al. |
| 5,879,314 A | 3/1999 | Peterson et al. |
| 5,879,364 A | 3/1999 | Bromfield et al. |
| 5,882,302 A | 3/1999 | Driscoll, Jr. et al. |
| 5,894,841 A | 4/1999 | Voges |
| 5,895,362 A | 4/1999 | Elstrom et al. |
| 5,947,921 A | 9/1999 | Johnson et al. |
| 5,960,792 A | 10/1999 | Lloyd et al. |
| 5,989,245 A | 11/1999 | Prescott |
| 6,001,069 A | 12/1999 | Tachibana et al. |
| 6,007,499 A | 12/1999 | Martin et al. |
| 6,014,970 A | 1/2000 | Ivri et al. |
| 6,024,718 A | 2/2000 | Chen et al. |
| 6,026,808 A | 2/2000 | Armer et al. |
| 6,027,495 A | 2/2000 | Miller |
| 6,041,253 A | 3/2000 | Kost et al. |
| 6,061,597 A | 5/2000 | Rieman et al. |
| 6,076,519 A | 6/2000 | Johnson |
| 6,083,159 A | 7/2000 | Driscoll, Jr. et al. |
| 6,095,141 A | 8/2000 | Armer et al. |
| 6,098,620 A | 8/2000 | Lloyd et al. |
| 6,102,298 A | 8/2000 | Bush et al. |
| 6,104,952 A | 8/2000 | Tu et al. |
| 6,106,547 A | 8/2000 | Huei-Jung |
| 6,113,558 A | 9/2000 | Rosenschein et al. |
| 6,113,570 A | 9/2000 | Siegel et al. |
| RE36,939 E | 10/2000 | Tachibana et al. |
| 6,158,431 A | 12/2000 | Poole |
| 6,176,839 B1 | 1/2001 | DeLuis et al. |
| 6,186,963 B1 | 2/2001 | Schwarze et al. |
| 6,190,315 B1 | 2/2001 | Kost et al. |
| 6,190,336 B1 | 2/2001 | Duarte et al. |
| 6,206,842 B1 | 3/2001 | Tu et al. |
| 6,206,843 B1 | 3/2001 | Iger et al. |
| 6,231,528 B1 | 5/2001 | Kaufman et al. |
| 6,234,990 B1 | 5/2001 | Rowe et al. |
| 6,251,099 B1 | 6/2001 | Kollias et al. |
| 6,273,864 B1 | 8/2001 | Duarte et al. |
| 6,296,630 B1 | 10/2001 | Altman et al. |
| 6,314,318 B1 * | 11/2001 | Petty .................. 607/2 |
| 6,321,109 B2 | 11/2001 | Ben-Haim et al. |
| 6,322,527 B1 | 11/2001 | Talish |
| 6,325,769 B1 | 12/2001 | Klopotek |
| 6,478,754 B1 * | 11/2002 | Babaev .................. 601/2 |
| 6,533,803 B2 * | 3/2003 | Babaev .................. 607/89 |
| 6,663,554 B2 * | 12/2003 | Babaev .................. 600/2 |
| 6,761,729 B2 * | 7/2004 | Babaev .................. 607/89 |

FOREIGN PATENT DOCUMENTS

| | | |
|---|---|---|
| EP | 0 437 155 B1 | 2/1990 |
| EP | 0 657 226 B1 | 11/1994 |
| GB | 2 099 710 A | 12/1982 |
| GB | 2 101 500 A | 1/1983 |
| JP | 2000237275 A2 | 9/2000 |
| WO | WO 96/35383 | 11/1996 |

OTHER PUBLICATIONS

Design and Application of Low-Frequency Ultrasound and Its Combination With Laser Radiation in Surgery and Therapy—Critical Reviews in Biomedical Engineering; 2001; pp. 502-519.

* cited by examiner

USING TRANSDUCER WITH CYLINDRICAL TIP

USING TRANSDUCER WITH INCREASED RADIATION SURFACE

ULTRASOUND WOUND TREATMENT METHOD AND DEVICE USING STANDING WAVES

FIELD OF INVENTION

The present invention relates to the treatment of wounds using ultrasound standing waves. In particular, the present invention relates to a method and device of creating ultrasonic standing waves in air and directing them to a wound for delivering aerodynamic forces as ultrasonic radiation pressure and ultrasonic waves as well. Ultrasound radiation pressure increases the blood flow in the wound area, and ultrasound waves kill bacteria, stimulate healthy tissue cells, and treat the wound.

BACKGROUND OF THE INVENTION

Ultrasonic waves have been widely used in medical applications, including diagnostics and therapy as well as many industrial applications, e.g., welding, cutting, fiber optics technology, speed meters, etc. Diagnostic use of ultrasound waves includes using ultrasonic waves to detect underlying structures in an object or human tissue. In this method, an ultrasonic transducer is placed in contact with the tissue or object via a coupling medium, and high frequency (1–10 MHz) ultrasonic waves are directed into the tissue. Upon contact with the various underlying structures, the waves are reflected back to a receiver adjacent the transducer. By comparison of the signals of the ultrasonic waves sent with the reflected ultrasonic wave as received, an image of the underlying structure can be produced. This technique is particularly useful for identifying boundaries between components of tissue and can be used to detect irregular masses, tumors, etc.

Three therapeutic medical uses of ultrasound waves include aerosol mist production, contact physiotherapy, and soft tissue ablation. The ultrasound contact physiotherapy procedure may cause a patient significant discomfort and/or pain, and skin may appear raw and damaged. Aerosol mist production makes use of a nebulizer or inhaler to produce an aerosol mist for creating a humid environment and delivering drugs to the lungs.

Ultrasonic nebulizers operate by passing ultrasound waves of sufficient intensity through a liquid, the waves being directed at an air-liquid interface of the liquid from a point underneath or within the liquid. Liquid particles are ejected from the surface of the liquid into the surrounding air following the disintegration of capillary waves produced by the ultrasound. This technique can produce a very fine dense fog or mist.

Aerosol mists produced by ultrasound are preferred because a smaller particle size of the aerosol can be obtained with the ultrasonic waves. One of the major shortcomings of ultrasonic inhalers and nebulizers is that there is no directed aerosol to the target. An air stream is then required to direct the aerosol to the target, but this decreases the efficiency of ultrasound.

Ultrasonic sprayers (Sonic and Materials Inc., Misonix Inc., Sono-Tek Inc., Zevex International, Inc., operate by passing liquid trough central orifice of ultrasound instrument-tip. See, for example, U.S. Pat. Nos. 3,765,606; 4,659,014; 5,104,042; 4,9307,00; 4,153,201; 4,655,393; 5,516,043; 5,835,678; 5,879,364; and 5,843,139.

Ultrasonic inhalers and drug delivery systems from Medisonic USA, Inc., 3M, Siemens Gmb, The Procter & Gamble Company, Sheffield Pharmaceuticals, Aradigm, Inc., operate by atomizing liquid using piezoceramic film. See, for example, U.S. Pat. Nos. 4,294,407; 5,347,998; 5,520,166; 5,960,792; 6,095,141; 6,102,298; 6,098,620; 6,026,808; and 6,106,547.

OBJECT OF THE INVENTION

It is an object of the invention to provide an improved method and device for treating wounds.

It is also an object of this invention to provide an improved method and device for treating wounds using ultrasound standing waves.

It is a further object of the invention to provide a method and device for increasing blood flow, killing bacteria, and stimulating healthy tissue cell growth.

These and other objects of the invention will become more apparent from the discussion below.

SUMMARY OF INVENTION

The present invention is a method and device for using ultrasonic standing waves to treat wounds. Ultrasound standing waves occur as a result of incident and reflected waves from a reflective surface that are traveling in opposite directions. The resultant superposition of the two waves forms standing waves, which create ultrasonic radiation pressure. The standing waves, actually ultrasound radiation pressure, occur when the distance between (a) the distal end of a transducer (as a radiant of ultrasound waves) and (b) the reflected surface (e.g., a wound surface) is: $n\times\lambda/2$, where $\lambda$ is the wave length and n is a positive integer. The standing waves are more effective in limited space or area as a tube.

According to the invention ultrasound waves are created, directed, and delivered to a wound surface through the air to increase blood flow, kill bacteria, stimulate healthy tissue cells and treat wounds with ultrasound energy. The method of treating wounds involves the use of ultrasound standing waves of a continuous or pulsed ultrasound.

More particularly, the method of the invention comprises producing ultrasound standing waves using a free end surface of an ultrasonic transducer and wound surface.

According to the method of the present invention, the radiation pressure of ultrasonic standing waves increase blood flow in wound area and destroy the surface bacteria to result in a higher disinfecting property of ultrasound. Additionally, the ultrasound also stimulates healthy cell growth to aid in granulization and epithelization of the healing tissue. Other applications of the method can be directed to non-medical uses such as cleansing, drying, sterilizing and coating surfaces of objects and food.

The method of the present invention offers an approach that may re-establish use of some traditional ultrasound and establish a method of treating wound and fighting bacteria without antibiotics when necessary.

The overall concept of the present invention relates in method and apparatus for wound treatment using ultrasonic standing waves through air with no drug. This wound treatment method is possible with combination of different energy sources as an ultrasound, laser, electric current, magnetic field, ultraviolet, microwaves, radio frequency, etc.

BRIEF DESCRIPTION OF DRAWINGS

FIG. 1 is a perspective view of an ultrasound wound treatment system with standing waves, according to the present invention;

FIG. 2 is a schematic, lateral cross-sectional view of another transducer useful with the system of FIG. 1.

DETAILED DESCRIPTION OF THE PREFERRED EMBODIMENTS

The present invention is a method and system, which uses ultrasound standing wave energy to treat wounds. The system comprises a generator of electrical signals and a handpiece having an ultrasound transducer and tip.

Figure 1:
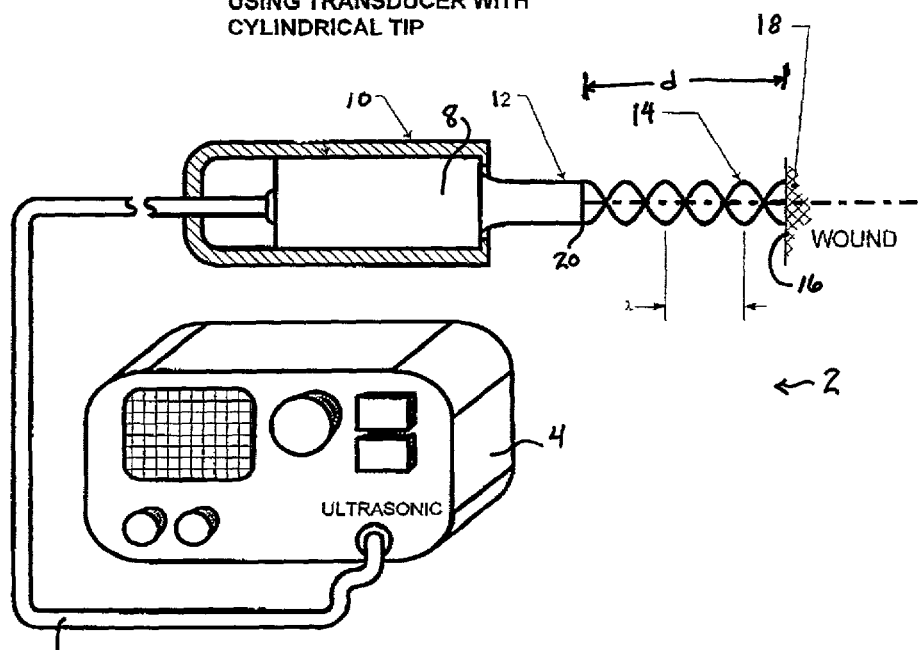
Figure 2:
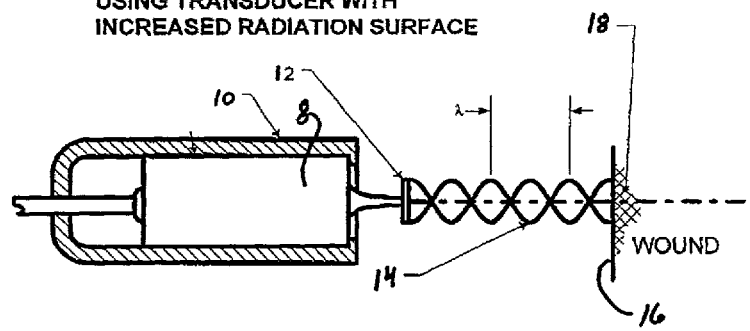

The invention can perhaps be better appreciated from the drawings. A system for wound treatment according to present invention is illustrated in FIG. 1. The system 2 comprises a signal generator 4 operatively or electrically connected through cable 6 to a transducer 8 in a housing 10. Transducer 8 has an ultrasound tip 12 that generates standing ultrasound waves 14. Standing ultrasound waves 14 are directed to the surface 16 of a wound 18.

Standing ultrasound waves 14 occur when activated ultrasound tip 12 is directed through the air to a wound surface 16 as a result of incident and reflected waves from wound surface 16, which creates ultrasonic radiation pressure. The distal end 20 of transducer tip 12 (as a radiant of ultrasound waves) is preferably a distance d from wound surface 16 (a source of reflected waves). Distance d is related to the wavelength λ of the ultrasound wave or signal by the formula $$d = n \times \lambda/2$$

where n is a positive integer. To reach this preferred distance and therefore effect wound treatment practice, ultrasound transducer 8 or tip 12 must frequently be moved back and forward toward wound surface 16 by an operator.

The waveform of the ultrasound waves generated by transducer 8 preferably corresponds to the waveform of the electrical signals generated by signal generator 4. For example, electrical signals from signal generator 4 with rectangular, sinusoidal, trapezoidal, or triangular waveforms will cause transducer 8 to produce respective similarly shaped ultrasound waveforms.

Figure 3:
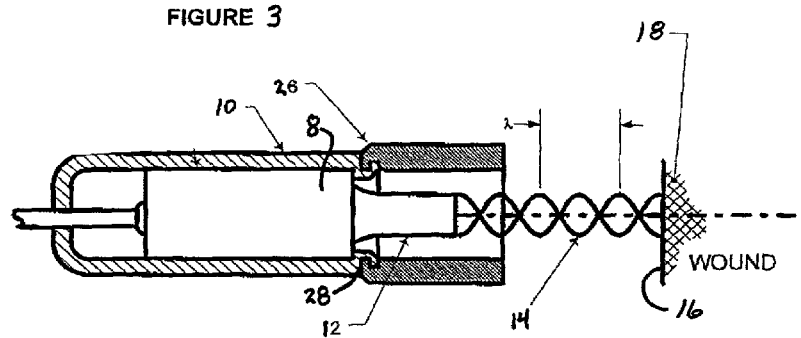
FIG. 3 is a schematic, lateral cross-sectional view of a transducer having a bushing.

The standing waves are more effective in limited space or area such as a tube. In each of FIGS. 3 to 5 a bushing 26 increases ultrasound radiation pressure. Bushing 26 may or may not be disposable part on the distal end 28 of housing 10.

Figure 4:
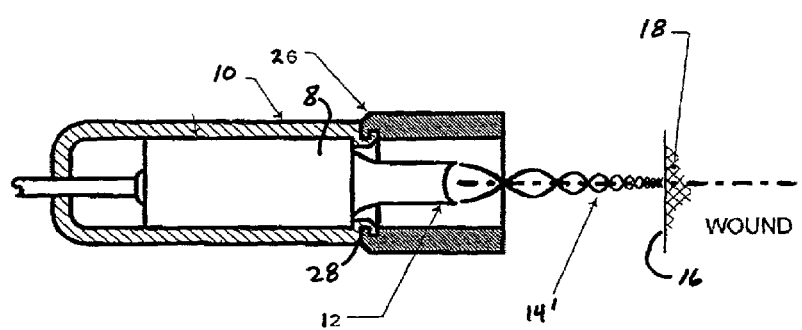
FIG. 4 is a schematic, lateral cross-sectional view of a transducer of FIG. 3 where the distal tip has been modified to provide a focussed beam.

In the embodiment of the invention set forth in FIG. 4 the distal end 28 of ultrasonic tip 12 has been modified to a concave shape to focus ultrasound waves 14'.

Figure 5:
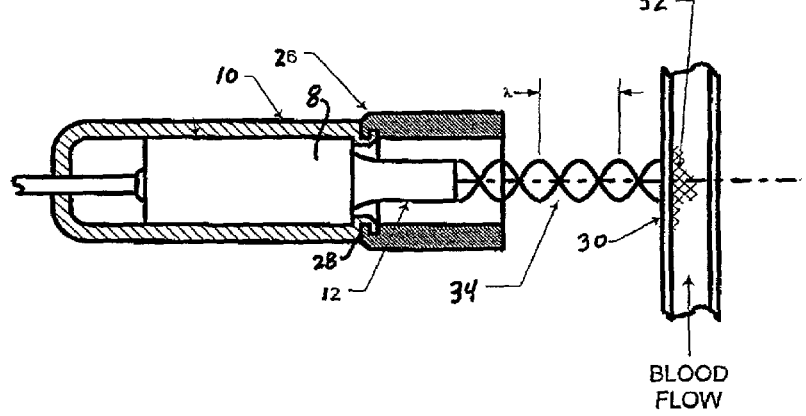
FIG. 5 is a schematic, lateral cross-sectional view of an embodiment of the invention intended to facilitate dissolution of blood clots.

One of the possible applications of the method of present invention is the facilitation of dissolution of blood clots by using ultrasound energy. In FIG. 5 ultrasound tip 12 is directed to a blood vessel 30 with clot or clots 32. In this case ultrasound standing waves 34 create cavitation inside blood vessel 30 and dissolve clot or clots 32.

In another embodiment of the present invention a wound can also be treated with a gel or drug. After the gel or drug is applied to the wound surface, ultrasound standing waves would be directed to the wound. The drug would be activated and penetrate into tissue under ultrasound radiation pressure.

Additional possible application of method using ultrasound standing waves is for the diffusion of grafts to a wound with radiation pressure gently.

It is provided that the ultrasound transducer operates at a frequency from 10 kHz to 10,000 MHz and the distance d is at least 0.1 inch.

The preceding specific embodiments are illustrative of the practice of the invention. It is to be understood, however, that other expedients known to those skilled in the art or disclosed herein may be employed without departing from the spirit of the invention or the scope of the appended claims.

I claim:

1. A method for treating an external wound from a non-contact distance d, comprising the steps of:
    positioning an ultrasound transducer such that a distal radiation surface of the ultrasound transducer is positioned at a distance substantially equal to the non-contact distance d from the surface of the external wound; and
    creating and maintaining ultrasound standing waves between the surface of the external wound and the distal radiation surface, wherein the ultrasound standing waves are created and maintained in air along the non-contact distance d, wherein the non-contact distance d is determined by the formula:

$$d = n \times \lambda/2,$$

where λ is the wavelength of an ultrasound standing wave and n is a positive integer, and wherein the ultrasound standing waves create radiation pressure for providing a bactericidal and a therapeutic effect to the external wound for decreasing the healing time for the external wound.

2. The method of claim 1, wherein the ultrasound transducer operates at a frequency of from about 10 kHz to $10^3$ MHz.

3. The method of claim 1, wherein the non-contact distance d is at least 0.1 inch.

4. The method of claim 1, wherein in a prior step a gel or drug is applied to the wound surface.

5. A method for treating an external wound from a non-contact distance comprising the steps of:
    providing a transducer having a distal radiation surface arranged at the non-contact distance from the surface of the external wound for emitting ultrasonic waves; and
    creating and maintaining ultrasound standing waves in air between the surface of the external wound and the distal radiation surface by adjusting the non-contact distance, wherein the ultrasound standing waves create radiation pressure for providing a bactericidal and a therapeutic effect to the external wound for decreasing the healing time for the external wound.

6. The method of claim 5, wherein the transducer operates at a frequency from 10 kHz to 10,000 MHz.

7. The method of claim 5, wherein the non-contact distance is at least 0.1 inch.

8. The method of claim 5, further comprising the steps of:
    driving the transducer by pulsed or modulated frequency; and
    selecting the driving wave form of the transducer from the group consisting of sinusoidal, rectangular, trapezoidal and triangular wave forms.

9. The method of claim 5, wherein the therapeutic effect is selected from the group consisting of increasing blood flow to the external wound, mechanically cleansing the external wound, dissolving blood clots within a vessel exposed as an external wound, diffusing grafts, stimulating cell growth, providing at least one medicament to the external wound, and penetrating at least one medicament through the surface of the external wound.

10. The method of claim 5, further comprising the steps of:
 applying a drug to the external wound; and
 penetrating the drug through the surface of the external wound using the radiation pressure created by the ultrasound standing waves.

11. The method of claim 5, further comprising the step of providing a bushing around the distal radiation surface for increasing the radiation pressure created by the ultrasound standing waves, wherein the non-contact distance is between a distal end of the bushing and the surface of the external wound.

12. The method of claim 5, further comprising the step of focusing the ultrasound waves.

* * * * *